United States Patent
Agnihotri et al.

(10) Patent No.: US 7,103,142 B1
(45) Date of Patent: Sep. 5, 2006

(54) MATERIAL ANALYSIS USING MULTIPLE X-RAY REFLECTOMETRY MODELS

(75) Inventors: Dileep Agnihotri, Round Rock, TX (US); Alex Dikopoltsev, Haifa (IL); Boris Yokhin, Nazareth Illit (IL)

(73) Assignee: Jordan Valley Applied Radiation Ltd., Migdal Ha'emek (IL)

( * ) Notice: Subject to any disclaimer, the term of this patent is extended or adjusted under 35 U.S.C. 154(b) by 0 days.

(21) Appl. No.: 11/065,737

(22) Filed: Feb. 24, 2005

(51) Int. Cl.
*G01T 1/36* (2006.01)

(52) U.S. Cl. .......................................... 378/82; 378/83
(58) Field of Classification Search ............... 378/82, 378/83
See application file for complete search history.

(56) References Cited

U.S. PATENT DOCUMENTS

| | | |
|---|---|---|
| 3,919,548 A | 11/1975 | Porter |
| 3,980,568 A | 9/1976 | Pitchford et al. |
| 4,048,496 A | 9/1977 | Albert |
| 4,725,963 A | 2/1988 | Taylor et al. |
| 4,916,720 A | 4/1990 | Yamamoto et al. |
| 5,003,569 A | 3/1991 | Okada et al. |
| 5,619,548 A | 4/1997 | Koppel |
| 5,740,226 A | 4/1998 | Komiya et al. |
| 5,923,720 A | 7/1999 | Barton et al. |
| 5,937,026 A | 8/1999 | Satoh |
| 6,041,095 A | 3/2000 | Yokhin |
| 6,108,398 A | 8/2000 | Mazor et al. |
| 6,192,103 B1 | 2/2001 | Wormington et al. |
| 6,381,303 B1 | 4/2002 | Vu et al. |
| 6,512,814 B1 | 1/2003 | Yokhin et al. |
| 6,704,661 B1* | 3/2004 | Opsal et al. ............... 702/27 |
| 6,754,305 B1 | 6/2004 | Rosencwaig et al. |
| 6,823,043 B1 | 11/2004 | Fewster et al. |
| 2003/0012337 A1* | 1/2003 | Fewster et al. ............... 378/86 |
| 2004/0267490 A1* | 12/2004 | Opsal et al. ............... 702/127 |

FOREIGN PATENT DOCUMENTS

| | | |
|---|---|---|
| EP | 0 423 803 B1 | 3/1997 |
| JP | 8-136479 | 5/1996 |
| JP | 8-220027 | 8/1996 |
| JP | 10-318737 | 12/1998 |
| JP | 10-325814 | 12/1998 |
| JP | 10-185846 | 9/1999 |

OTHER PUBLICATIONS

Leng, J.M. et al. "Simultaneous measurement of six layers in a silicon on insulator film stack using spectrophotometry and beam profile reflectometry" J. Appl.Phys. 81 (8), Apr. 15, 1997, pp. 3570-3578.*

(Continued)

*Primary Examiner*—Edward J. Glick
*Assistant Examiner*—Krystyna Suchecki
(74) *Attorney, Agent, or Firm*—Christie, Parker & Hale, LLP.

(57) ABSTRACT

A method for inspection of a sample includes irradiating the sample with a beam of X-rays, measuring a distribution of the X-rays that are emitted from the sample responsively to the beam, thereby generating an X-ray spectrum, and applying a multi-step analysis to the spectrum so as to determine one or more physical properties of a simulated model of the sample. The multi-step analysis includes spectrally analyzing the spectrum so as to determine one or more characteristic frequencies and fitting the simulated model to the spectrum by an iterative optimization process beginning from an initial condition determined by the one or more characteristic frequencies.

30 Claims, 7 Drawing Sheets

OTHER PUBLICATIONS

Dane, et al., *Application of genetic algorithms for characterization of thin layered materials by glancing incidence X-ray reflectometry,* Physica B 253, 1998, pp. 254-268.

Huang, et al., *Characterization of single-And Multiple-Layer Films By X-Ray Reflectometry,* Advances in X-Ray Analysis, vol. 35, 1992, pp. 137-142.

Naudon et al., *New Apparatus for Grazing X-ray Reflectometry in the Angle-Resolved Dispersive Mode,* Journal of Applied Crystallography 22 (1989) pp. 460-464.

Lengeler, *X-ray Relection, a New Tool for Investigating Layered Structures and Interfaces,* Advances in X-ray Analysis 35 (1992), pp. 127-136.

Leenaers et al., *Applications of Glancing Incidence X-ray Analysis,* X-ray Spectrometry 26 (1997), pp. 115-121.

Wiener et al., *Characterization of Titanium Nitride Layers by Grazing-Emission X-ray Flourescence Spectrometry,* Applied Surface Science 125 (1998), pp. 129-136.

Windover et al., *Thin Film Density Determination by Multiple Radiation Energy Dispersive X-ray Reflectivity,* 47th Annual Denver X-ray Conference (Aug. 1998).

Funahasi et al., *BST Thin Film Evaluation Using X-ray Flourescense and Reflectivity Method,* 47th Annual Denver X-ray Conference (Aug. 1998), 1 page.

Remmel et al., *Development of an XRF Metrology Method for Composition and Thickness of Barium Strontium Titanate Thin Films,* 47th Annual Denver X-ray Conference (Aug. 1998), 1 page.

Radtke, et al., *A New Position Sensitive Detector for X-ray Diffractometry,* Advances in X-Ray Analysis, vol. 36, J. V. Gilfrich et al Eds; Plenum Press, New York, 1993, pp. 617-622.

G.M. Zorn, *The New Siemens X-ray Reflectometer. A Tool with Outstanding Capabilities,* Siemens Analytical Application No. 337; Mar. 1994.

*Fast X-ray Reflectometry Tool for Film Thickness Measurement,* AIMA Laboratories, Technical Note R02, 1999.

Verman, et al., *Confocal Graded d-Spacing Multilayer Beam Conditioning Optics,* 47th Annual Denver X-ray Conference (Aug. 1998), 1 page.

A.E. Braun, *Multipoint X-Ray Reflectometry Faster, Cost Effective,* Inspection, Measurement & Test, Semiconductor International, Feb. 1998, 2 pages.

Terada, S., *Introduction To SMAT200 Film Thickness Gauge,* Technos Co., Ltd., Mar. 23, 1998, 9 pages (previously listed as On Order).

\* cited by examiner

THICKNESS A

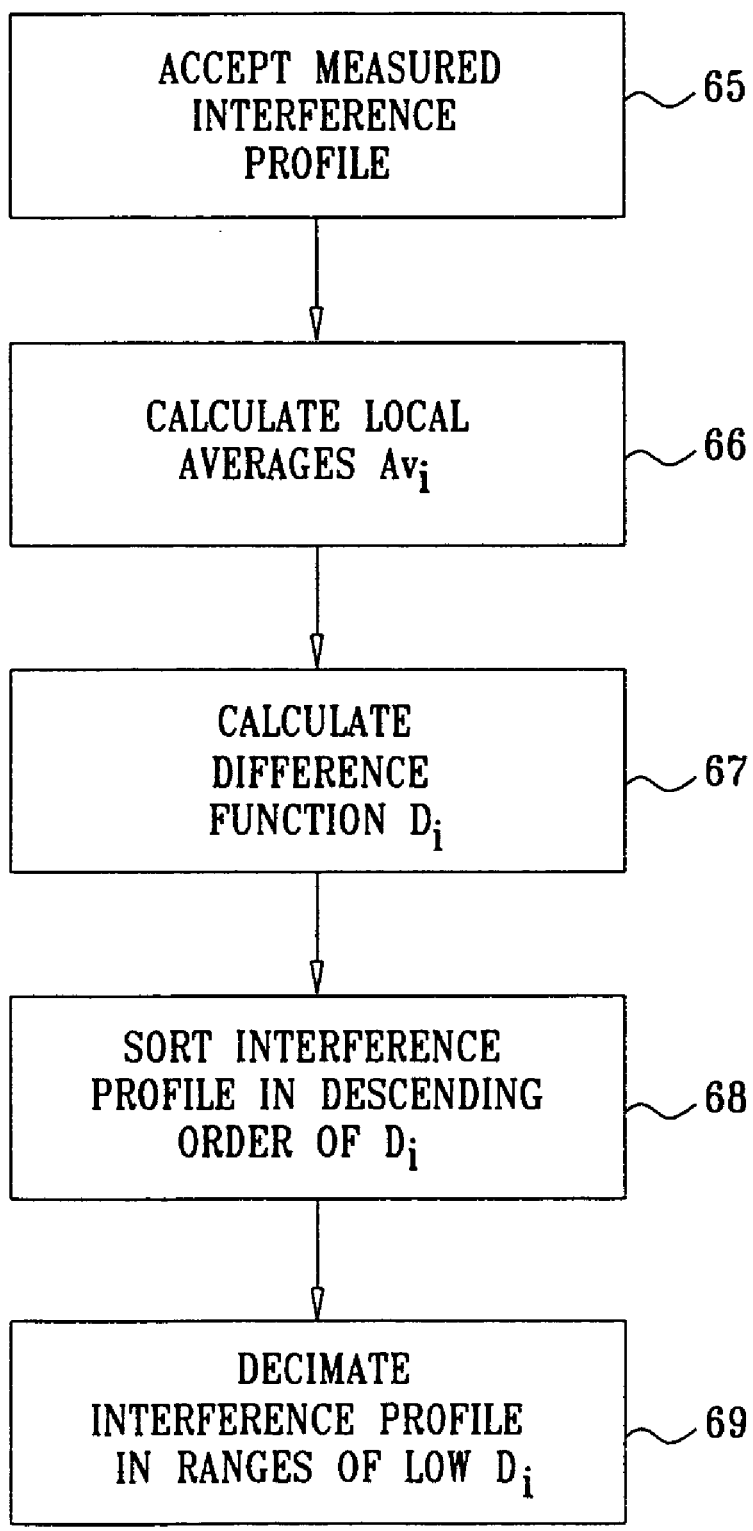

MATERIAL ANALYSIS USING MULTIPLE X-RAY REFLECTOMETRY MODELS

FIELD OF THE INVENTION

The present invention relates generally to X-ray reflectometry, and specifically to methods and systems for thin film analysis using X-rays.

BACKGROUND OF THE INVENTION

X-ray reflectometry (XRR) is a well-known technique for measuring the thickness, density and surface quality of thin film layers deposited on a substrate. X-ray reflectometers typically operate by irradiating a sample with a beam of X-rays at grazing incidence, i.e., at a small angle relative to the surface of the sample, near the total external reflection angle of the sample material. Measurement of X-ray intensity reflected from the sample as a function of angle gives a profile of interference fringes, which is analyzed to determine the properties of the film layers responsible for creating the fringe profile. Several X-ray reflectometers have been described in the patent literature, such as U.S. Pat. Nos. 6,512,814, 5,619,548 and 5,923,720, whose disclosures are incorporated herein by reference.

Various methods have been developed for analyzing measured interference profiles and fitting them to simulated models, as will be explained in detail hereinbelow. Some model fitting methods use Fourier transform analysis, particularly for measuring sample thickness. For example, U.S. Pat. No. 6,754,305, whose disclosure is incorporated herein by reference, describes a method for finding the layer thicknesses of a wafer using a Fourier transform analysis. U.S. Pat. No. 5,740,226, whose disclosure is incorporated herein by reference, describes a film thickness measuring method comprising the steps of measuring reflectance of X-rays on a film, extracting interference oscillations from the measured X-ray reflectance, and Fourier transforming the interference oscillations to compute a film thickness of the film.

Some of the proposed methods for fitting the model to the measured data involve Genetic Algorithms (GA) or Evolutionary Algorithms (EA). A genetic algorithm is an optimization algorithm based on the mechanisms of evolution which uses random mutation, crossover and natural selection procedures to "breed" better models or solutions from an initial condition. For example, U.S. Pat. No. 6,192,103, whose disclosure is incorporated herein by reference, describes the use of evolutionary algorithms to find a global solution to the fitting of experimental X-ray scattering data to simulated models.

Dane et al. describe the use of known genetic algorithms for the characterization of materials in a paper entitled "Application of Genetic Algorithms for Characterization of Thin Layered Materials by Glancing Incidence X-Ray Reflectometry," Physica B, volume 253 (1998), pages 254–268, which is incorporated herein by reference. The genetic algorithm is used during the process of comparing two x-ray profiles and modifying of a calculated profile. The authors state that the proposed genetic algorithm is able to find good fits within a single run, reducing the amount of human effort and expertise required for analysis.

Other model fitting methods known in the art employ exhaustive searching. For example, U.S. Pat. No. 6,192,103, cited above, describes an approach known in the art, in which the parameter space is divided into small, but finite, regions. An error function is calculated for each region, and the region that produces the smallest error value is chosen as the best-fit parameter vector. In a related approach, mentioned in the same patent, known as the Monte Carlo method, the parameter space is again divided into small regions. The regions are selected at random, and the error function is evaluated for each. After a certain number of regions have been chosen, or when the error value is smaller than a specified value, the search is stopped. The region with the smallest error value is chosen as the best fit.

U.S. Pat. No. 6,823,043, whose disclosure is incorporated herein by reference, describes a method for determining parameters of a material by fitting a model to an experimental X-ray scattering profile. Fitting is performed on a selected sub-range of the scattering profile and gradually extended to cover the entire profile. Several fitting methods are proposed, including a genetic algorithm.

Other model fitting methods known in the art are based on gradient methods, such as the Levenberg-Marquardt method. For example, U.S. Pat. Nos. 6,754,305 and 6,512,814, cited above, describe the use of the Levenberg-Marquardt method for XRR model fitting.

SUMMARY OF THE INVENTION

Embodiments of the present invention provide methods and systems for analyzing XRR measurements to find properties of a sample using a sequence of different model fitting methods. These embodiments are useful in reducing the calculation time needed for XRR analysis and minimizing the required human involvement and expertise. These features of the present invention thus enable fast, automated analysis, as required by applications such as production line testing in semiconductor fabs. In some semiconductor fab applications, the disclosed methods may be used to provide a real-time alert in case of process failure. This type of alert increases the overall yield of the process and avoids loss of material and the associated cost.

In methods of model fitting that are conventionally used in analyzing XRR spectra, a simulated interference profile (i.e., a simulated XRR spectrum) is generated based on a simulated model of the sample, and is then compared with the measured spectrum. The parameters of the simulated model are then modified iteratively until the simulated interference profile fits the measured spectrum. Several limitations may be encountered when using individually any one of the model fitting methods described above:

1. Long calculation time: Some of the fitting methods require a long calculation time in order to converge to a solution. In addition, the calculation time typically depends on the choice of initial conditions (initial model parameters). Individual fitting methods typically begin with random or arbitrary initial conditions, or an initial condition entered by a user, based on his or her prior knowledge of the sample. The choice of initial conditions may have a significant effect on the calculation time.

2. False local minima: The best-fitting model sought by the optimization method may be viewed as the global minimum of an error function, assigning an error value to each set of model parameters, as a measure of the model's proximity to the measured sample. However, the error function is typically a highly non-linear function and in many practical cases comprises local minima in addition to the global minimum that reflects the true solution to the fitting problem. These local minima represent false solutions corresponding to non-optimal fitting of the model. Some of the currently-available fitting methods are prone to convergence to false local minima. Again, convergence to a false solution may depend on the choice of initial conditions.

3. Low precision: Some currently-available fitting methods converge to the proximity of the global minimum, but do not reach the absolute minimum. This residual error may be due to a large iteration step-size or other resolution limitation.

4. Limited parameter range: Some currently-available fitting methods may operate only over a limited range of measured parameters. For example, a genetic algorithm is typically limited to a range on the order of ±30% around the nominal thickness, ±20% around the nominal density and ±50% around the nominal surface roughness of the sample. In many practical cases the required range of parameters is significantly larger. For example, in some applications the layer thickness may vary in the range of 30 Å to 1000 Å.

Furthermore, it is well known in the art that each model fitting method has characteristic advantages and limitations. Using the right combination of fitting methods in the correct order enables the advantages of each method to be exploited while avoiding its limitations. For example, genetic algorithms are typically slow to converge when operating over large parameter spaces, but are useful for optimizing the fit in a particular angular range when given an approximate model as initial condition. FFT-based methods, on the other hand, typically provide coarse precision but are useful for quick approximation of a model over a large parameter space. Levenberg-Marquardt and other gradient-based methods are useful for achieving a final high-precision fit given an approximate solution.

Using a sequence of two or more fitting methods also enables narrowing of the parameter space required for searching, thereby reducing the calculation time and increasing the probability of convergence to the correct solution. For example, sample thickness is measured by focusing on a particular angular range in the interference profile, referred to as the "oscillation range," which shows a characteristic pattern of periodic oscillations. The angular frequency of these oscillations is inversely proportional to the thickness of the sample or one of its layers. A sequence of fitting methods may begin with identifying the relevant oscillation range using an FFT-based method, then performing a GA fit only within the oscillation range.

Some embodiments of the present invention also use different FOMs (Figures-Of-Merit) in the fitting process for quantifying the agreement between the simulated interference profile and the measured XRR spectrum. Using different FOMs in a single fitting sequence provides a better ability to extract information regarding different material layers and helps to avoid false local minima, as will be explained below.

Embodiments of the present invention resolve some of the aforementioned drawbacks by utilizing different model fitting methods in a single analysis sequence. Several exemplary analysis sequences are described hereinbelow.

There is therefore provided, in accordance with an embodiment of the present invention, a method for inspection of a sample, including:

irradiating the sample with a beam of X-rays;

measuring a distribution of the X-rays that are emitted from the sample responsively to the beam, thereby generating an X-ray spectrum; and applying a multi-step analysis to the spectrum so as to determine one or more physical properties of a simulated model of the sample, the analysis including:

spectrally analyzing the spectrum so as to determine one or more characteristic frequencies; and fitting the simulated model to the spectrum by an iterative optimization process beginning from an initial condition determined by the one or more characteristic frequencies.

In a disclosed embodiment, measuring the distribution includes measuring an X-ray reflectance spectrum, and applying the multi-step analysis includes determining at least one of a thickness, a density and a surface quality of one or more surface layers on the sample.

In another embodiment, spectrally analyzing the spectrum includes applying a Fourier Transform analysis method. Additionally or alternatively, the iterative optimization process includes at least one of a gradient-based algorithm and an exhaustive search algorithm. Further additionally or alternatively, the iterative optimization process includes a genetic algorithm.

In yet another disclosed embodiment, fitting the simulated model includes applying two or more genetic algorithm processes to give respective fitting results, and includes comparing the respective fitting results in order to determine the physical properties.

In still another embodiment, applying the multi-step analysis includes reducing a volume of data in the X-ray spectrum so as to generate a compressed spectrum, and then fitting the simulated model to the compressed spectrum.

In another embodiment, fitting the simulated model includes applying two or more different FOM (Figure-Of-Merit) functions to the spectrum and to the simulated model. Additionally or alternatively, fitting the simulated model includes applying a FOM function that is corrected for aberrations and statistics of a system used to irradiate the sample and measure the distribution.

In a disclosed embodiment, applying the multi-step analysis includes exchanging external data with at least one of an optical ellipsometer and an X-ray fluorescence spectrometer.

There is also provided, in accordance with an embodiment of the present invention, a method for inspection of a sample that includes one or more thin film layers, including:

irradiating the sample with a beam of X-rays;

measuring a distribution of the X-rays that are emitted from the sample responsively to the beam, thereby generating an X-ray spectrum;

applying an optical ellipsometer to measure a characteristic of at least one of the thin film layers; and fitting a simulated model to the spectrum by an iterative optimization process, beginning from an initial condition determined by the characteristic measured by the optical ellipsometer, so as to determine one or more physical properties of the sample.

There is additionally provided, in accordance with an embodiment of the present invention, a method for inspection of a sample that includes one or more thin film layers, including:

irradiating the sample with a beam of X-rays;

measuring a distribution of the X-rays that are reflected from the sample responsively to the beam, thereby generating an X-ray spectrum;

applying an X-ray fluorescence (XRF) detector to measure a characteristic of at least one of the thin film layers; and fitting a simulated model to the spectrum by an iterative optimization process, beginning from an initial condition determined by the characteristic measured by the XRF detector, so as to determine one or more physical properties of the sample.

There is further provided, in accordance with an embodiment of the present invention, a method for inspection of a sample, including:

irradiating the sample with a beam of X-rays;

measuring a distribution of the X-rays that are emitted from the sample responsively to the beam, thereby generating an X-ray spectrum; and applying a multi-step analysis to the spectrum so as to determine one or more physical properties of simulated models of the sample, the analysis including:

fitting the simulated model to the spectrum by two or more iterative optimization processes so as to generate respective fitting results; and comparing the results of the two or more iterative optimization processes so as to determine an output model of the multi-step analysis.

In a disclosed embodiment, fitting the simulated model includes applying a genetic algorithm. In another embodiment, fitting the simulated model includes applying two or more genetic algorithm processes to give the respective fitting results. Additionally or alternatively, comparing the results includes applying an additional genetic algorithm process to the fitting results, so as to determine the output model.

In another disclosed embodiment, fitting the simulated model includes applying a different, respective FOM (Figure-Of-Merit) function in each of at least two of the iterative optimization processes.

There is also provided, in accordance with an embodiment of the present invention, a method for inspection of a sample, including:

irradiating the sample with a beam of X-rays measuring a distribution of the X-rays that are emitted from the sample responsively to the beam, thereby generating an X-ray spectrum; and applying a multi-step analysis to the spectrum so as to determine one or more physical properties of a simulated model of the sample, the analysis including:

selectively reducing a volume of data in the spectrum so as to generate a compressed spectrum; and fitting the simulated model to the compressed spectrum by an iterative optimization process.

In a disclosed embodiment, selectively reducing the volume of the data includes identifying one or more ranges in the spectrum that exhibit a low variability, and selectively decimating the data in the one or more angular ranges.

Additionally or alternatively, identifying the ranges includes calculating a local average of data points in the spectrum, evaluating respective distances of the data points from the local average, and removing a portion of the data points for which the respective distances are less than a chosen threshold.

There is additionally provided, in accordance with an embodiment of the present invention, apparatus for inspection of a sample, including:

an X-ray source, which is arranged to irradiate the sample with a beam of X-rays;

a detector assembly, which is arranged to measure a distribution of the X-rays that are emitted from the sample responsively to the beam, thereby generating an X-ray spectrum; and a processor, which is arranged to spectrally analyze the spectrum so as to determine one or more characteristic frequencies, and to fit a simulated model to the spectrum by an iterative optimization process beginning from an initial condition determined by the one or more characteristic frequencies, thereby determining one or more physical properties of the simulated model of the sample.

There is further provided, in accordance with an embodiment of the present invention, apparatus for inspection of a sample that includes one or more thin film layers, including:

an X-ray source, which is arranged to irradiate the sample with a beam of X-rays;

a detector assembly, which is arranged to measure a distribution of the X-rays that are emitted from the sample responsively to the beam, thereby generating an X-ray spectrum; and a processor, which is arranged to receive a measurement from an optical ellipsometer of a characteristic of at least one of the thin film layers, and to fit a simulated model to the spectrum by an iterative optimization process, beginning from an initial condition determined by the characteristic measured by the optical ellipsometer, so as to determine one or more physical properties of the sample.

There is additionally provided, in accordance with an embodiment of the present invention, apparatus for inspection of a sample that includes one or more thin film layers, including:

an X-ray source, which is arranged to irradiate the sample with a beam of X-rays;

a detector assembly, which is arranged to measure a distribution of the X-rays that are reflected from the sample responsively to the beam, thereby generating an X-ray spectrum; and a processor, which is arranged to receive a measurement from an X-ray fluorescence (XRF) detector of a characteristic of at least one of the thin film layers, and to fit a simulated model to the spectrum by an iterative optimization process, beginning from an initial condition determined by the characteristic measured by the XRF detector, so as to determine one or more physical properties of the sample.

There is also provided, in accordance with an embodiment of the present invention, apparatus for inspection of a sample, including:

an X-ray source, which is arranged to irradiate the sample with a beam of X-rays;

a detector assembly, which is arranged to measure a distribution of the X-rays that are emitted from the sample responsively to the beam, thereby generating an X-ray spectrum; and a processor, which is arranged to fit a simulated model to the spectrum by two or more iterative optimization processes so as to generate respective fitting results and to compare the results of the two or more iterative optimization processes, thereby determining one or more physical properties of the simulated model of the sample.

There is also provided, in accordance with an embodiment of the present invention, apparatus for inspection of a sample, including:

an X-ray source, which is arranged to irradiate the sample with a beam of X-rays;

a detector assembly, which is arranged to measure a distribution of the X-rays that are emitted from the sample responsively to the beam, thereby generating an X-ray spectrum; and a processor, which is arranged to selectively reduce a volume of data in the spectrum so as to generate a compressed spectrum and to fit a simulated model to the compressed spectrum by an iterative optimization process.

There is further provided, in accordance with an embodiment of the present invention, a computer software product for analyzing an X-ray spectrum, the product including a computer-readable medium in which program instructions are stored, which instructions, when read by a computer, cause the computer to spectrally analyze the spectrum so as to determine one or more characteristic frequencies, and to fit a simulated model to the spectrum by an iterative optimization process beginning from an initial condition determined by the one or more characteristic frequencies, thereby determining one or more physical properties of the simulated model of the sample.

The present invention will be more fully understood from the following detailed description of the embodiments thereof, taken together with the drawings in which:

BRIEF DESCRIPTION OF THE DRAWINGS

FIG. 4 is a flow chart that schematically illustrates a method for data compression, in accordance with an embodiment of the present invention.

DETAILED DESCRIPTION OF EMBODIMENTS

XRR System Description

Figure 1:
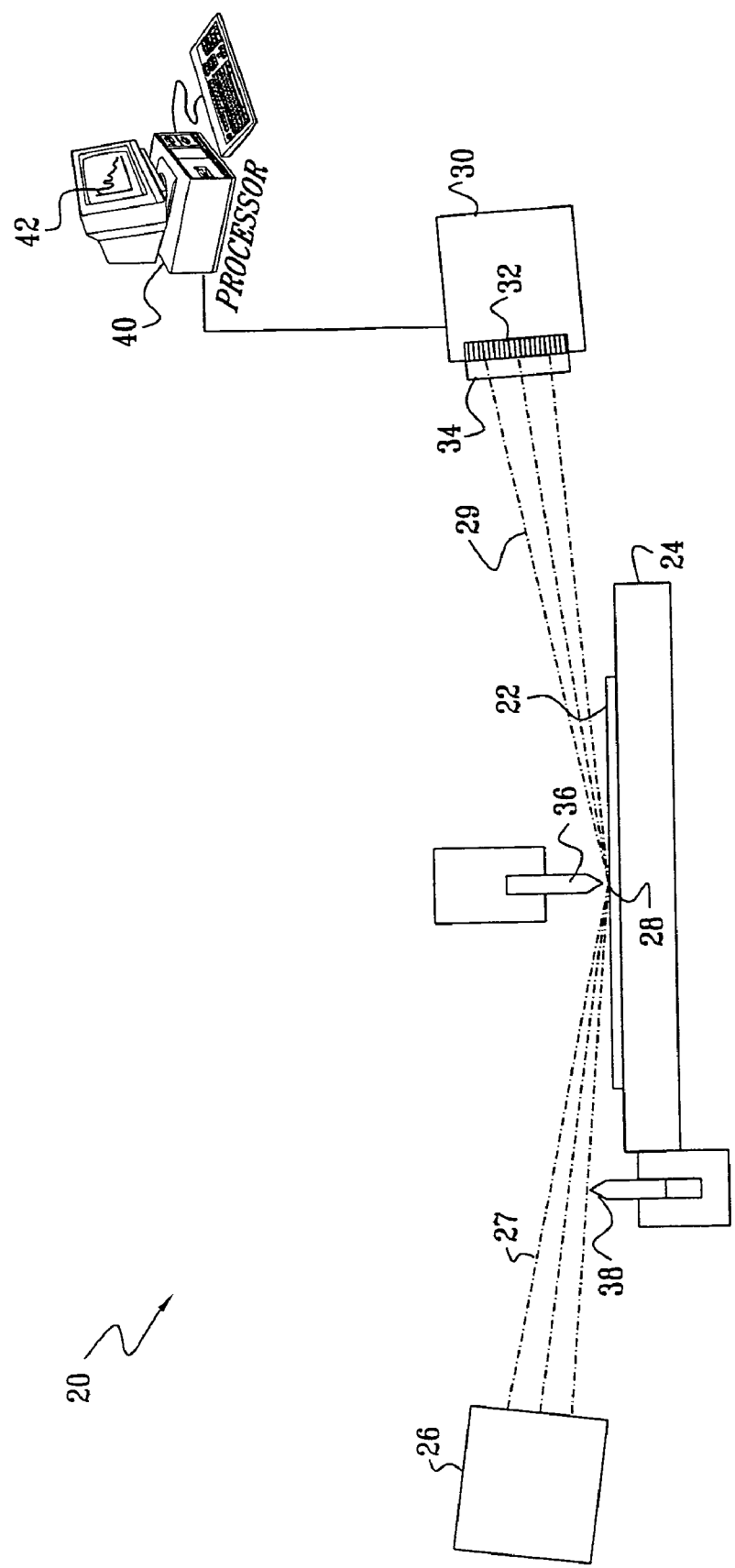
FIG. 1 is a schematic illustration of a system for X-ray reflectometry, in accordance with an embodiment of the present invention.

FIG. 1 is a schematic illustration of a system 20 for X-ray reflectometry (XRR) of a sample 22, in accordance with an embodiment of the present invention. The sample is typically mounted on a motion stage 24, allowing accurate adjustment of its position and orientation. An X-ray source 26 irradiates a small area 28 on sample 22. A dynamic knife edge 36 and a shutter 38 may be used to limit an incident beam 27 of the X-rays, as described in the above-mentioned U.S. Pat. No. 6,512,814.

A reflected beam 29 of X-rays from sample 22 is collected by a detector assembly 30. Typically, assembly 30 collects reflected X-rays over a range of reflection angles between about 0° and 5°, both below and above the critical angle of the sample for total external reflection. Assembly 30 comprises a detector array 32, typically arranged in either a linear or a matrix (two-dimensional) array.

A reflectometry processor 40 analyzes the output of assembly 30, so as to determine an X-ray spectrum comprising an interference profile 42 of the flux of X-ray photons reflected from sample 22 as a function of angle. Typically, sample 22 has one or more thin surface layers, such as thin films, at area 28, so that interference profile 42 exhibits an oscillatory structure due to interference effects among reflected X-ray waves from the interfaces between the layers. The processor analyzes characteristics of the oscillatory structure in order to determine the thickness, density and surface quality of one or more of the surface layers, using methods of analysis described herein.

Typically, processor 40 comprises a general-purpose computer processor, which performs the functions described hereinbelow under the control of suitable software. This software may be downloaded to the processor in electronic form, over a network, for example, or it may alternatively be provided on tangible media, such as optical, magnetic or non-volatile electronic memory. Further alternatively, the functions described hereinbelow may be implemented in dedicated hardware logic, or using a combination of hardware and software elements.

Reflectometry processor 40 may be implemented as a standalone unit, or it may alternatively be integrated with a semiconductor production and/or test equipment setup or other platform. Further alternatively, the functions of processor 40 may be distributed among several separate computing platforms.

Model Fitting Sequences

FIGS. 2A–2F are block diagrams that schematically show typical model fitting sequences performed by processor 40 in accordance with embodiments of the present invention. In a typical model fitting sequence, processor 40 receives measured interference profile 42 and an initial condition (i.e., a set of initial model parameters entered by the user). The processor then performs a sequence of model fitting methods, as constructed by the user, wherein the solution generated by each fitting method is used as an initial condition to the next fitting method. The processor ultimately produces an output model. The output model is a simulated model of the properties of the surface layer or layers of sample 22, such as the layer densities, thickness and surface quality, such that the interference profile of the output model closely resembles measured interference profile 42.

A graphical user interface of processor 40 enables a user to arrange the various individual model fitting methods as modular building blocks. The user may arrange the blocks in different ways to construct different computational sequences. Additional building blocks comprise input and output blocks, as well as a block for evaluating and comparing solutions. The following list describes the building blocks available to the user of processor 40 for constructing different model fitting sequences:

Input block 50: The first block of every sequence, comprising validity testing of input data, data normalization and filtering.

Output block 52: The final block of every sequence, comprising presentation and interpretation of the output model.

FFT (Fast Fourier Transform) block 54: An FFT-based model-fitting method, which receives an input sample sequence and outputs spectral coefficients. (In the present embodiment, the input sample sequence comprises amplitude samples of a measured XRR spectrum as a function of angle, and the spectral coefficients correspond to the angular frequency components of the spectrum, referred to herein as "characteristic frequencies," which give an indication of the thickness of a surface layer or layers on the sample.) The inventors have implemented an FFT-based fitting method that is described in detail in U.S. Pat. No. 6,512,814, cited above. Alternatively, any suitable FFT-based method known in the art, such as the methods referenced hereinabove, may be used for implementing this block.

GA (Genetic Algorithm) block 56: An optimization method based on a genetic algorithm. Block 56 receives a sample sequence, such as a measured XRR spectrum, and a set of initial parameter values, such as the estimated thickness of one or more surface layers, along with nominal layer densities and surface quality. Block 56 then applies a GA algorithm to adjust the parameter values until the simulated spectrum produced by a sample with the adjusted parameter values optimally fits the actual input spectrum. Any suitable GA-based method, including the methods cited and referenced hereinabove, may be used for this purpose. A GA fit may be invoked two or more times within a sequence, for example in order to optimize the model fitting in particular angular ranges of the interference profile, wherein each GA fit is limited to operate in a partial angular range. Additionally, GA block 56 may comprise a method for data compression for further reducing the required calculation time, as will be explained in detail below.

Comparator block 58: A block for comparing different solutions, as generated by any fitting method, and selecting the best solution according to a predetermined criterion or function. The fitting criterion is also referred to as a FOM (Figure-Of-Merit). The selected solution serves as the output model of the entire sequence or as an initial condition to a subsequent fitting step in the sequence.

Levenberg-Marquardt block (not shown in the figures): A gradient-based fitting method, typically used for "fine-tuning," or fine optimization of the fit in a relatively small parameter space. Any suitable gradient-based method known in the art may be used for implementing this block.

Exhaustive search block (also referred to as a "brute-force" block, not shown in the figures): A block implementing an exhaustive search of a given parameter space and angular range. The exhaustive search is assured to find the global minimum and is useful for obtaining a precise result with assured accuracy, as long as the range to be searched in sufficiently small. (Otherwise, the amount of time required to conduct the exhaustive search may be prohibitive.) The exhaustive search may be used for final refinement of model parameters after other techniques have been used to narrow the search range. This block is typically used for fitting one or two parameters in a narrow angular range. For example, this method may be used for density determination in the "critical angular" range of the interference profile or for thickness determination in the "oscillation" range of the profile.

Ellipsometry import/export block (not shown in the figures): A block for exchanging measured data with an optical ellipsometer. Operation of the ellipsometer itself is outside the scope of this patent application, and any suitable ellipsometer may be used in conjunction with this block. The ellipsometer may either comprise an external unit or be integrated as part of reflectometry system 20. Ellipsometers can typically measure the thickness and refractive index of a layer with high accuracy, while illuminating a substantially smaller spot size than area 28 of sample 22 that is shown in FIG. 1 above. This ability is useful, for example, for focusing on a specific device, such as a transistor, on a semiconductor wafer. On the other hand, ellipsometers typically require calibration using a non-drifting reference measurement of the sample. Exporting of calculated thickness data from reflectometry processor 40 to the ellipsometer may provide such calibration. Thickness data imported from the ellipsometer to reflectometry processor 40 may be used as a highly-accurate initial condition to the various fitting blocks.

XRF (X-ray fluorescence spectroscopy) import/export block (not shown in the figures): A block for exchanging measured data with an XRF spectrometer. Operation of the spectrometer itself is outside the scope of this patent application, and any suitable spectrometer may be used in conjunction with this block. (An exemplary XRF system is described in U.S. Pat. No. 6,041,095, whose disclosure is incorporated herein by reference.) The spectrometer may either comprise an external unit or be integrated as part of reflectometry system 20, as described, for example, in U.S. Pat. No. 6,381,303, whose disclosure is also incorporated herein by reference. An XRF spectrometer can typically measure the "surface density" of a layer (i.e., the layer thickness multiplied by its density) with high accuracy, while irradiating a substantially smaller spot size than area 28 of sample 22 that is shown in FIG. 1 above. Exporting XRR data from reflectometry processor 40 to the XRF spectrometer may be used for calibration of the spectrometer, eliminating the use of special XRF standard calibration samples. Surface density data imported from the XRF spectrometer to reflectometry processor 40 may be used as a highly-accurate initial condition to the various fitting blocks, such as the GA block described above. Good fitting of the XRR spectrum, in turn, can provide more accurate calibration of the XRF spectrometer.

Figure 2A:
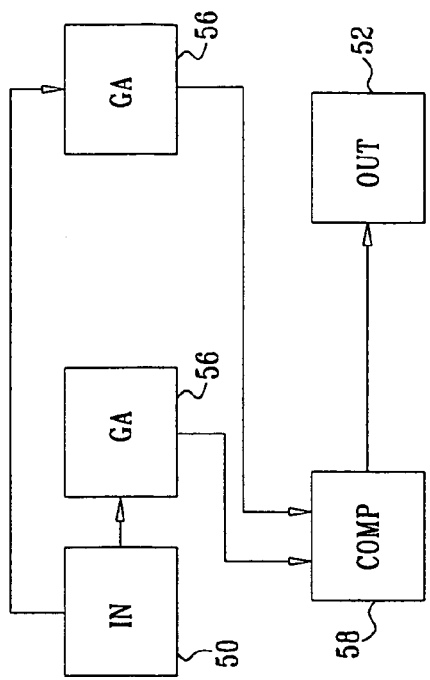
FIGS. 2A–2F are block diagrams that schematically show model calculation sequences in accordance with embodiments of the present invention.

FIGS. 2A–2F show the following exemplary sequences, which are constructed using the building blocks listed above:

FIG. 2A shows an example of a sequence comprising FFT block 54, followed by GA block 56. This sequence is typical for generating a "coarse approximation" model using the FFT-based fitting method, then using the coarse model as an initial condition for the genetic algorithm fitting method. The range about the initial condition over which the model parameters are permitted to vary during the operation of GA block 56 may also be restricted in order to reduce the time required for the genetic algorithm to run.

Figure 2B:
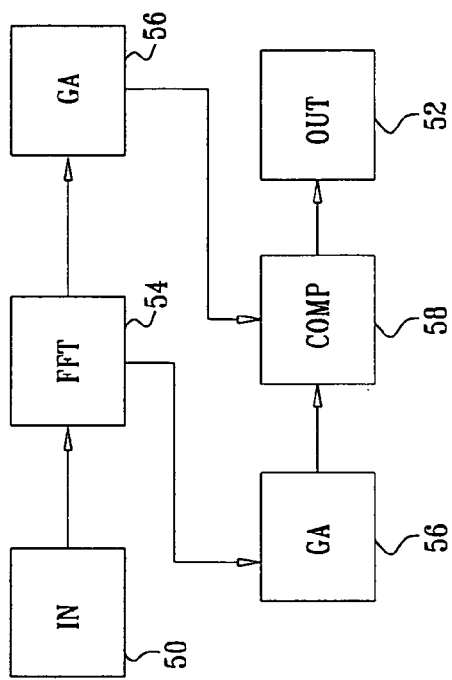

FIG. 2B shows an example of a sequence in which two GA blocks 56 are applied to the same input data. (The GA blocks are conceptually shown in parallel, although the actual computations in the two blocks may be performed serially.) Typically, each GA fit uses different initial conditions. Alternatively, the two GA fits may start with the same initial conditions, since genetic algorithms include an element of randomization, and even two runs with the same initial conditions may give different results when the field of optimization includes multiple minima.

GA block 56 is applied twice in the sequence of FIG. 2B in order to detect and avoid situations in which processor 40 returns an incorrect set of model parameters because the GA converged to a local minimum of the optimization function, rather than to the global minimum. Assuming the likelihood of convergence to such a local minimum to be some small fraction $\epsilon$ (such as 1%), the likelihood that the GA will converge twice to the same local minimum is $\epsilon^2$ (0.01% in the present example). Therefore, if both GA blocks 56 in the sequence of FIG. 2B converge to the same model parameters, the parameters may be assumed to be correct with high confidence. Comparator block 58 compares the two resulting models generated by blocks 56 and outputs the solution if the models agree. If the models disagree, the comparator block may output the model parameters that give the best fit to the input data or, alternatively, an error message. In the latter case, the process of FIG. 2B may be repeated.

Figure 2C:
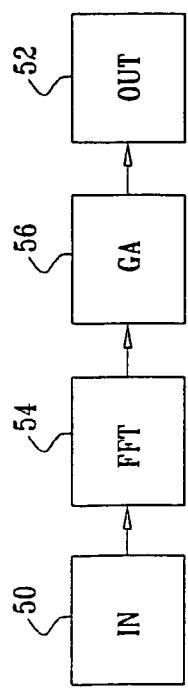

FIG. 2C shows another example of a sequence comprising two GA blocks 56 in parallel, followed by comparison of the solutions using comparator block 58. The solution chosen by block 58 may be used as an initial condition for an additional GA block 56, using a different set of parameters, a different physical model or a different FOM. The initial GA blocks are used to gain rough parameter estimation, typically using a simplified physical model, a small number of generations in the genetic algorithm and a reduced angular range. The better-fitting solution of the two initial GA blocks is selected by comparator block 58. The second GA block typically calculates a fully sophisticated model over the full angular range, but with small parameter ranges, as determined by the first GA blocks.

Figure 2D:
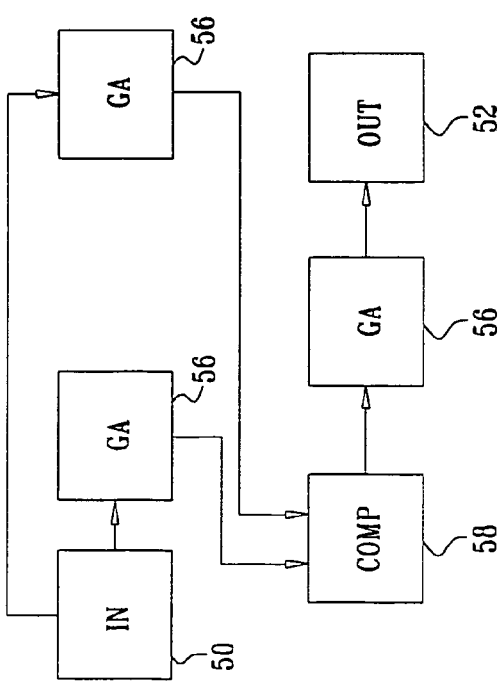

FIG. 2D shows an example of a sequence comprising an initial FFT block 50, followed by two parallel GA blocks 56 with the previous FFT result used as an initial condition. Comparator block 58 compares the two GA results in order to determine the best solution, as explained above in reference to FIG. 2B.

Figure 2E:
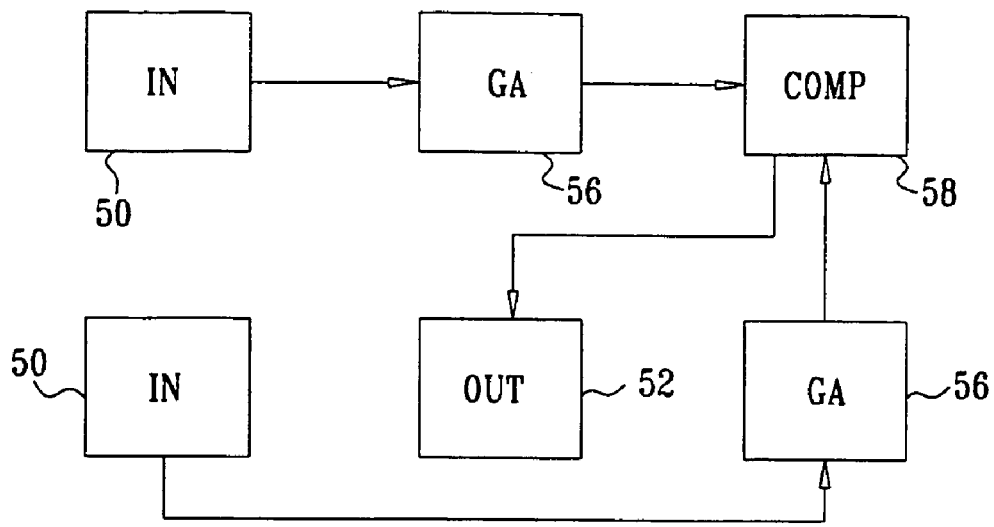

FIG. 2E shows an example of a sequence comprising two parallel input blocks 50, allowing different models and normalization conditions, followed by two parallel GA blocks 56. Comparator block 58 compares the results of the two GA blocks in order to determine the best solution (and the best model, if two different models are used in the two GA blocks), as explained above in the description of FIG. 2B.

Figure 2F:
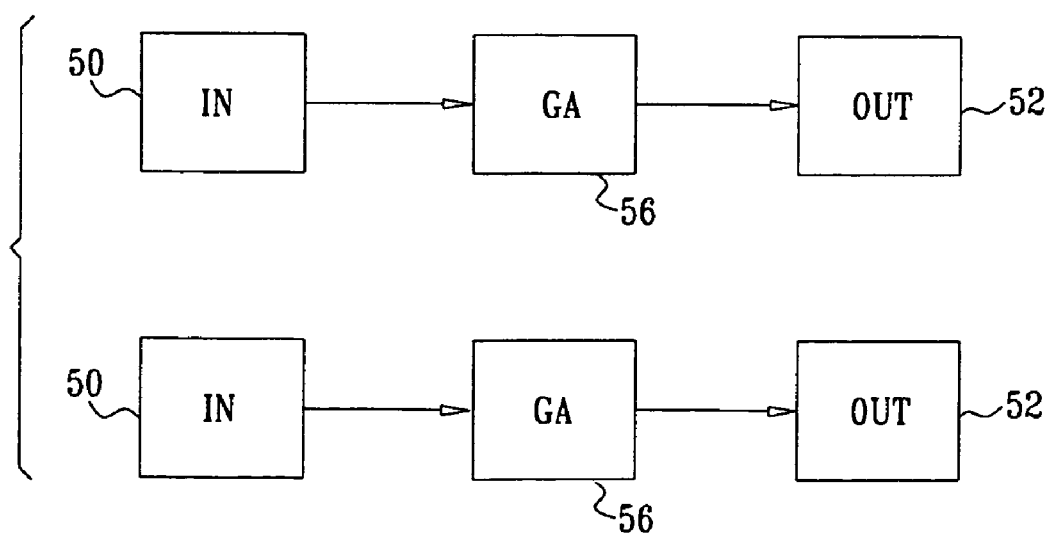

Finally, FIG. 2F shows an example of a sequence comprising two parallel fits to the same measured interference profile. (This approach is also referred to a "multimodel" fit.) Input blocks 50 allow similar or different physical models and normalization conditions. The input blocks are followed by two parallel GA blocks 56 and two parallel output blocks 52. The two fits provide two independent solutions. The two solutions may be used for estimating the solution stability. For example, the probability $\epsilon$ of convergence to a local minimum may be estimated, as explained in the description of FIG. 2B above.

The six fitting sequences described above are shown as illustrative examples for demonstrating the general method of using configurable multi-method sequences. Other sequence structures based on the tools described above, as well as sequences comprising additional fitting methods such as gradient-based fits and exhaustive searches, will be apparent to those skilled in the art.

FOM Functions

As mentioned above, the agreement between the simulated interference profile and the measured interference profile is quantified using a FOM function. The various model fitting blocks described above typically use the FOM function as a criterion in the optimization process. In addition, comparator block 58 uses the FOM to compare the results of two fitting blocks.

Any suitable FOM may be used in embodiments of the present invention. The inventors typically use the following six FOM functions. For each FOM function given below, R denotes the calculated FOM value, and N denoted the number of angular data points. $I_{m,i}$ and $I_{o,i}$ denote the intensities of the two interference profiles (wherein m stands for the "main" [simulated] profile, and o stands for the "overlay" [measured] profile, and i is a running index indicating the reflection angle):

1. SPEC—Standard spectrum comparison.

$$R = \frac{1}{N} \sum_i |\log I_{m,i} - \log I_{o,i}|$$

2. SQ2—logarithmic chi-square.

$$R = \sqrt{\frac{\sum_i (\log I_{m,i} - \log I_{o,i})^2}{N}}$$

3. SQ1—Weighted logarithmic chi-square.

$$R = \sqrt{\frac{\sum_i (\log I_{m,i} - \log I_{o,i})^2}{\sum_i (\log I_{o,i})^2}}$$

The SQ1 and SQ2 FOMs are also described by Huang and Parrish in a paper entitled "Characterization of Single- and Multi-Layer Films by X-Ray Reflectometry," Advances in X-Ray Analysis, volume 35, Plenum Press, New York, 1992, pages 137–142, which is incorporated herein by reference.

4. SMOOTH—"Smoothed" spectral comparison.

$$R = \left| \frac{1}{N} \sum_i (\log I_{m,i} - \log I_{o,i}) \right|$$

5. CAS—Corrected for Aberrations and Statistics. The CAS FOM is typically used in conjunction with a double acquisition process. The small-angle range of the interference profile, up to an angle denoted s, is acquired first using a short acquisition time. Then, shutter 38 is set to block angles smaller than s, and the remaining angular range is acquired using k times longer acquisition time. The two acquisition passes are then merged, and the result is denoted Y. While merging, the intensities in the small-angle range are multiplied by k for normalization. For statistical error estimation the values are converted back to the original, non-normalized values.

$$R = \frac{1}{N} \sum_i \left\{ \begin{array}{l} \ln 10 \sqrt{\frac{\pi}{2}} \sqrt{I_{o,i}} |\log I_{o,i} - \log I_{m,i}|, \ldots I_{o,i} < 2/(\pi \beta^2) \\ (\ln 10 / \beta) \cdot |\log I_{o,i} - \log I_{m,i}|, \ldots I_{o,i} \geq 2/(\pi \beta^2) \end{array} \right\}$$

wherein $$I_{o,i} = \left\{ \begin{array}{l} Y_{o,i}, \ldots i \geq s \\ (Y_{o,i}/k), \ldots i < s \end{array} \right\},$$

β is a measure of the beam aberration (uniformity) level, k denotes the factor of difference in acquisition times, and s is an index indicating the position of shutter 38. These parameters are determined empirically depending on the characteristics of the XRR system.

6. CASO—Statistical, similar to CAS but with β=0. Does not account for aberrations and uses a single acquisition pass.

$$R = \frac{\ln 10 \sqrt{\frac{\pi}{2}}}{N} \sum_i \left( \sqrt{I_{o,i}} \, |\log I_{m,i} - \log I_{o,i}| \right)$$

Different FOM functions may be used by different blocks in a single sequence to extract information regarding different layers of the sample. For example, when analyzing a Cu/Ta (Copper-Tantalum) sample, the CAS function is most robust for measuring the thickness and density of the copper layer. On the other hand, the SPEC function is more accurate for measuring tantalum and tantalum nitride (TaN) layers, as well as for distinguishing between the Ta and TaN layers, which have similar densities and are otherwise difficult to differentiate.

Model Fitting Example

Figure 3A:
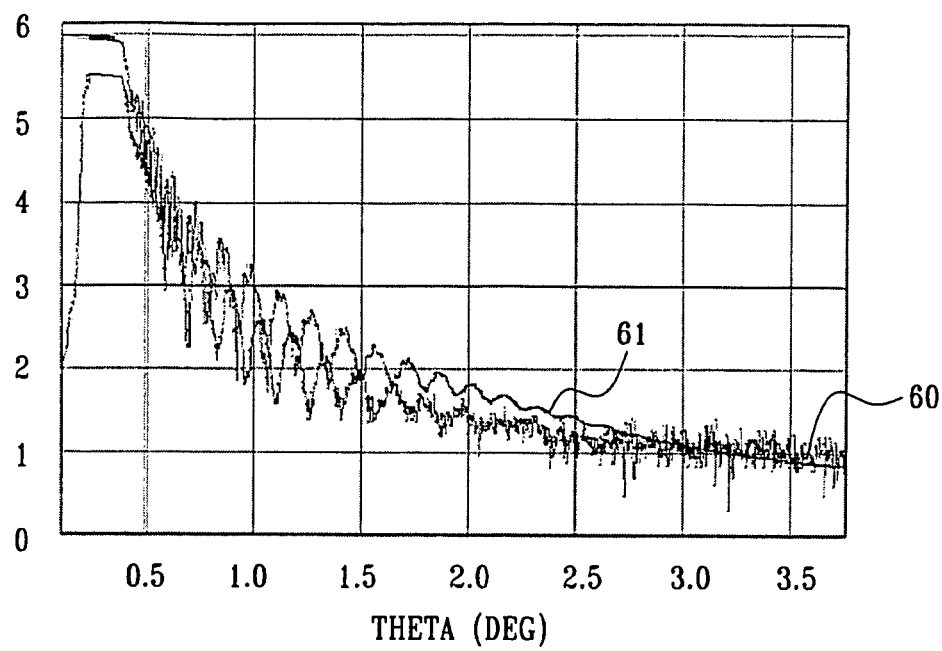
FIGS. 3A–3D are plots that schematically show the fitting of a model to experimental data, in accordance with an embodiment of the present invention.

FIG. 3A is a plot that schematically shows a measured XRR spectrum 60 captured by system 20 (FIG. 1), along with a curve 61 that is initially fitted to the spectrum, in accordance with an embodiment of the present invention. Sample 22 in this example comprises layers of copper oxide (CuO), copper (Cu), tantalum (Ta), tantalum nitride (TaN) and underlying layers formed on a silicon substrate. Nominal layer properties, as assumed by the fabrication process, are entered as initial conditions of the simulated model using input block 50 at the beginning of the sequence. The simulated interference profile corresponding to these initial conditions is shown by curve 61. The values are given in the following table:

| Layer | Thickness (Å) | Density (g/cm$^3$) | Roughness (Å) |
|---|---|---|---|
| CuO | 20 | 5 | 10 |
| Cu | 1000 | 8.9 | 12 |
| Ta | 120 | 16 | 7 |
| TaN | 160 | 15 | 8 |
| TaSi$_2$ | 20 | 3.5 | 2 |
| Si | Substrate | 2.33 | 3 |

From visual comparison of spectrum 60 and curve 61 in FIG. 3A, it can be seen that both curves show characteristic oscillations but are not congruent, indicating that the initial conditions do not fit the measured XRR signal.

In the present example, processor 40 uses the fitting sequence shown in FIG. 2D, comprising an FFT fit followed by two parallel GA fits. In this sequence, the solution generated by FFT block 54 serves as an initial condition for two parallel GA blocks 56, whose results are compared using comparator 58. The output model, representing the best solution to which the GA fits converged, is provided by processor 40 to the user using output block 52.

Figure 3B:
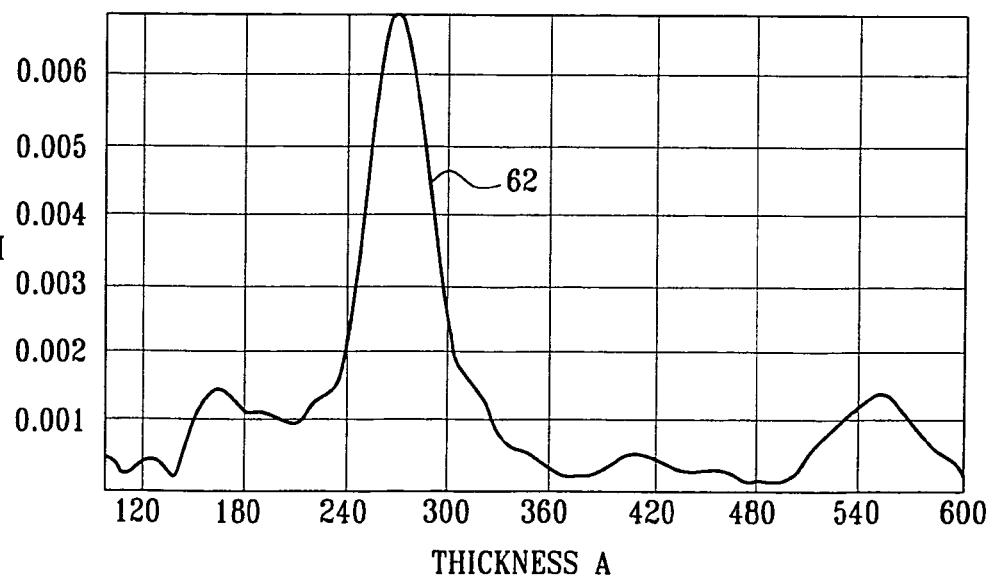

FIG. 3B is a plot that schematically shows a frequency spectrum produced by FFT block 54, in accordance with an embodiment of the present invention. The horizontal scale is normalized in units of layer thickness, instead of the original angular frequency units. The plot shows one of the peaks in the multi-peak FFT spectrum produced by FFT block 54, estimating the combined thickness of the tantalum (Ta) and tantalum nitride (TaN) layers of sample 22. This FFT spectrum was evaluated over the angular range 0.7°–2°, which is the "oscillation range" (i.e., the range of the interference profile that shows characteristic oscillations with angular frequency corresponding to the respective layer thickness) of the combined Ta+TaN layers. The spectrum shown in FIG. 3B indicates an estimated layer thickness of 269 Å (Angstrom) with a critical angle of 0.472°. The FFT block in this example was not able to differentiate between the Ta and TaN layers of sample 22, because of the similarity in the density of the two layers. The oscillations in the measured interference profile show a characteristic angular frequency that corresponds only to the combined thickness of the two layers. As will be shown later in this example, the subsequent GA block is able to differentiate between the two layers.

Figure 3C:
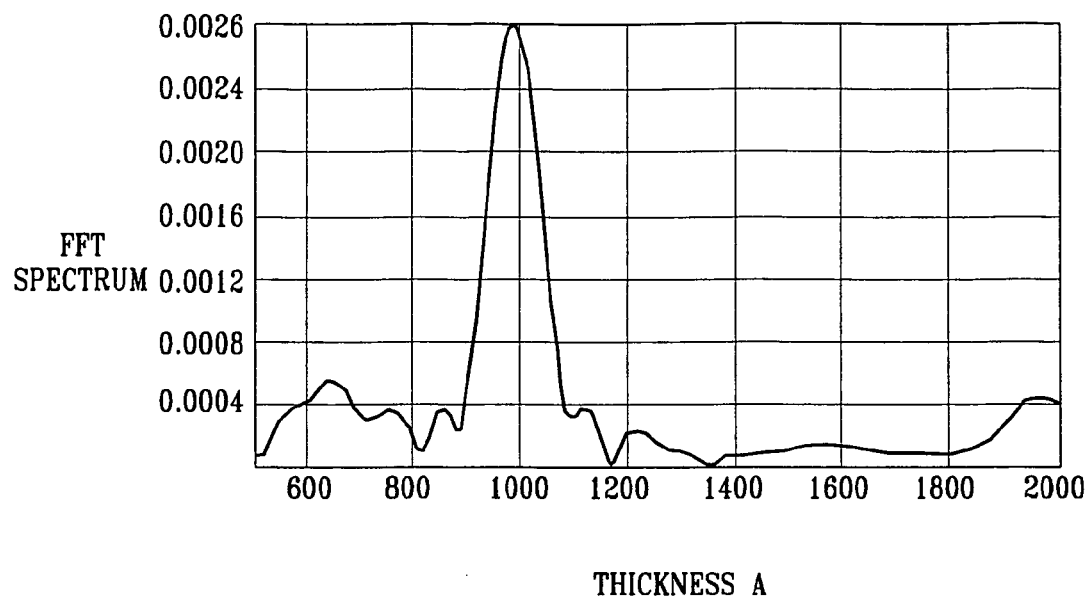

FIG. 3C is a plot that schematically shows another frequency spectrum produced by FFT block 54, in accordance with an embodiment of the present invention. The horizontal scale is again normalized in units of layer thickness. The plot shows a peak in the multi-peak FFT spectrum produced by FFT block 54, estimating the combined thickness of the copper (Cu) and copper oxide (CuO) layers of sample 22. This FFT spectrum was evaluated in the angular range 0.405°–0.8°, which is the oscillation range for the copper layer, with a critical angle of 0.405°. The spectrum shown in FIG. 3C indicates an estimated combined thickness of 982 Å for the CuO+Cu layers.

The following table shows the estimated layer thickness values, as calculated by FFT block 54 in the present example:

| Layer | Estimated Thickness (Å) |
|---|---|
| CuO* | 20 |
| Cu + CuO | 982 − 20 = 962 |
| Ta | 269 * 0.4 = 107.6 |
| TaN | 269 * 0.6 = 161.4 |
| TaSi$_2$* | 20 |

(* denotes technician estimates. The Ta layer thickness is assumed to comprise 40% of the combined estimated Ta+TaN thickness. The TaN layer thickness is assumed to comprise the remaining 60%.)

Following the FFT fitting, processor 40 performs two parallel GA fittings. The estimated layer thicknesses calculated by the preceding FFT fitting are used as initial conditions to the genetic algorithm. Several external preconditions may be incorporated into the GA initial conditions by the user, to enable the GA fit to differentiate between the Ta and TaN layers and between the Cu and CuO layers in spite of the poor contrast that was noted above. In this example, an initial thickness estimate of 20 Å was assumed for the CuO and TaSi$_2$ layers. The thickness of the Ta layer was assumed to be 40% of the combined estimated Ta+TaN thickness, or 107.6 Å. The TaN layer thickness was assumed to be the remaining 60%, or 161.4 Å. The following parameter space is defined for the GA fittings:

Thickness: FFT fitting estimate ±5%.
Density: Nominal input values ±20%.
Roughness: Nominal input values ±50%.

The two GA fittings in the present example converged to identical solutions. Therefore, comparator block 58 determines that the total fitting sequence is successful and provides the final set of parameters of the simulated interference profile to output block 52. The final estimated layer properties of sample 22 following the sequence of the present example is given in the following table:

| Layer | Thickness (Å) | Density (g/cm³) | Roughness (Å) |
|---|---|---|---|
| CuO | 20.5 | 3.665 | 11.9 |
| Cu | 966.6 | 8.993 | 14.3 |
| Ta | 99.6 | 16.131 | 7.0 |
| TaN | 164.4 | 14.777 | 4.3 |
| TaSi$_2$ | 22.4 | 3.244 | 2.7 |
| Si | Substrate | 2.33 | 1.0 |

Figure 3D:
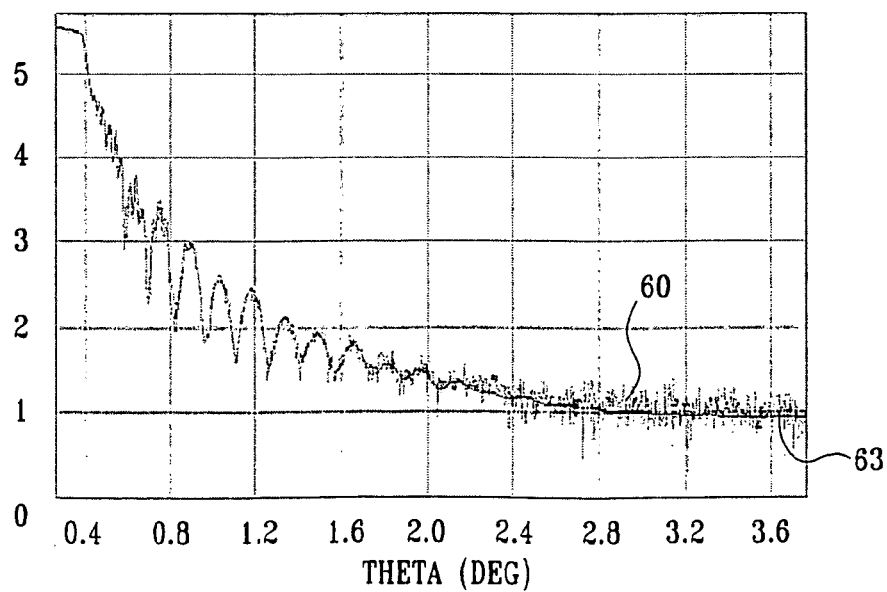

FIG. 3D is a plot that schematically shows the final fitting of the output model to the measured XRR signal 60, in accordance with an embodiment of the present invention. A curve 63 shows the simulated interference profile generated by the output model, as calculated by processor 40 using the disclosed method. It can be seen that curves 60 and 63 show very close resemblance, indicating a successful fitting of the model.

Data Compression Method

As mentioned above, one of the major limitations of some model fitting methods is the long calculation time required. In some embodiments of the present invention, reflectometry processor 40 is part of a semiconductor production line testing setup, or other on-line application in which it is important to reduce the calculation time. One way of reducing the calculation time is to reduce the number of angular data points in the interference profile of sample 22.

Embodiments of the present invention provide methods for eliminating part of the angular data points from interference profile 42, while maintaining high accuracy and reliability. The method is referred to as "data compression."

In one embodiment the method may be implemented manually, by visually inspecting the interference profile and identifying angular ranges characterized by slow changes. The number of angular data points may be reduced in these angular ranges.

In another embodiment the method may be implemented as an automatic method performed by reflectometry processor 40. The method identifies regions of the interference profile of relatively little variability, so that a portion of the data points in the region can be represented as a mean of the neighboring data points without substantial loss of information. The spectrum is then automatically decimated in these regions. Typically, the number of data points to remove is determined by the target data volume of the spectrum. Alternatively, the number is determined by an information loss threshold. Areas in the interference profile that exhibit high variability ("high-frequency data") remain untouched and preserve their original angular resolution.

The inventors have implemented the automatic data compression method described below, for reducing the number of angular data points.

Reference is now made to FIG. 4, which is a flow chart that schematically illustrates a method for data compression, in accordance with an embodiment of the present invention. The method begins with processor 40 accepting a measured interference profile at an input step 65. The interference profile comprises N angular data points denoted $Ex_i$, i=1, 2,,N. For each data point $Ex_i$, processor 40 defines a local average $Av_i$ at an averaging step 66. The local average is defined as:

$$Av_i = \sum_{j=i-1}^{i+1} \log(Ex_j)/3$$

$Av_i$ averages the current data point with its two nearest neighbors. Note that the interference profile is typically presented on a logarithmic scale, hence the "log" function inside the averaging formula.

Processor 40 subsequently defines a difference function $D_i$ describing the normalized difference of each data point from its corresponding local average, at a difference defining step 67. The difference function is defined as:

$$D_i = |Av_i - \log(Ex_i)| \cdot \sqrt{Ex_i}$$

Low $D_i$ values correspond to angular ranges characterized by low variability. Such areas are likely candidates for data compression, as the resulting loss of information is small.

Processor 40 next sorts the data points in descending order of $D_i$ at a sorting step 68. Finally, the processor applies data compression by decimation of the data points with values of $D_i$ that are lower than a given threshold, at a decimation step 69. The low-variance data points are decimated according to a predetermined decimation ratio. For example, if the decimation ratio is 1:3, then every third low-variance data point is preserved, while the rest are discarded. The threshold value for $D_i$ and the decimation ratio are typically chosen so that sufficient data points are discarded in order to reach the desired data volume.

The remaining angular data points, following decimation step 69, constitute a compressed interference profile, or compressed spectrum, having reduced angular resolution in angular ranges that exhibit low variability. The compressed interference profile may be used by processor 40 as input data to any model fitting method, including the methods described and referenced hereinabove. Because of the reduced number of data points, the computational burden involved in optimization methods such as genetic algorithms is reduced, and the speed of execution increases accordingly.

Figure 5A:
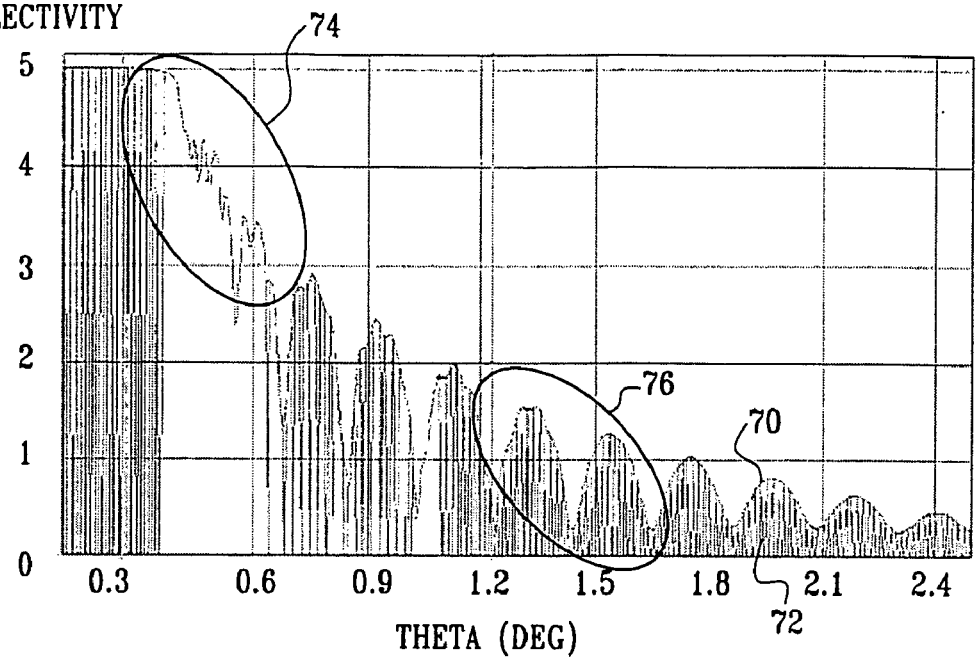
FIGS. 5A and 5B are plots that schematically illustrate a method for data compression, in accordance with an embodiment of the present invention.
Figure 5B:
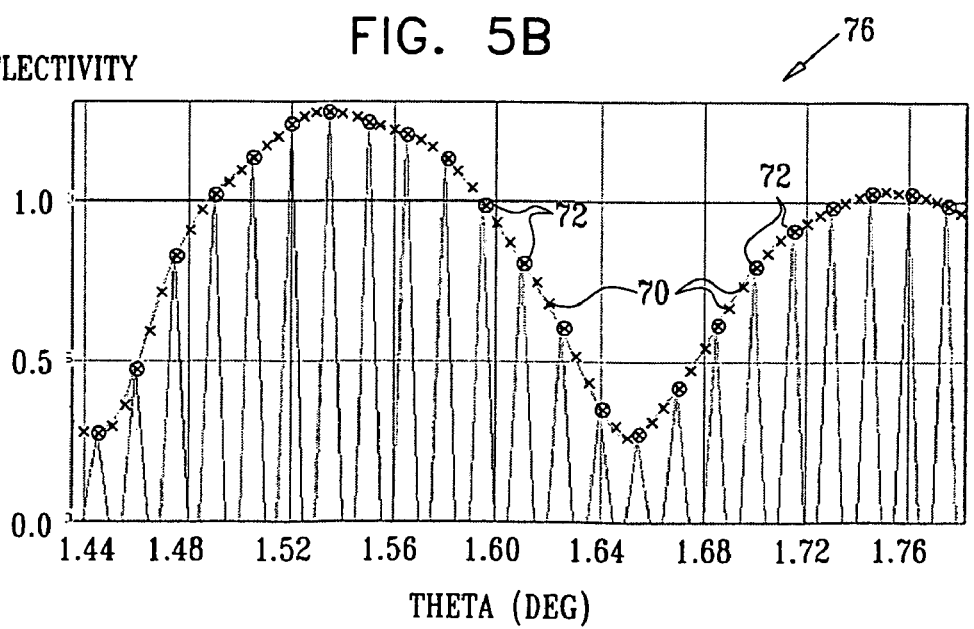

FIGS. 5A and 5B are plots that schematically illustrate application of the data compression method described above to the measurement of a silicon sample with copper and tantalum surface layers. FIG. 5A shows a measured interference curve 70 and a compressed interference curve 72 calculated by processor 40 using the automatic data compression method described above. A compression threshold of 50% was used in the present example. The angular data points of the measured interference profile were divided into points that require the full original angular resolution, such as a high-variability range 74, and points that do not require full resolution, such as a low-variability range 76. Ranges such as range 76 were compressed by the method, preserving only every third data point in these ranges.

FIG. 5B shows an enlarged view of low-variability range 76, enabling a clear view of measured interference profile 70

(with data points marked by x symbols) and of the compressed interference profile of curve 72 (with data points marked by ⓧ symbols).

Although the present patent application is concerned mainly with XRR systems, the model fitting and data compression methods disclosed herein may be equally applied to other metrology applications, such as X-ray scattering and X-ray diffraction, as well as applications using radiation in other spectral ranges. It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A method for inspection of a sample, comprising:
   irradiating the sample with a beam of X-rays;
   measuring a distribution of the X-rays that are emitted from the sample responsively to the beam, thereby generating an X-ray spectrum; and
   applying a multi-step analysis to the spectrum so as to determine one or more physical properties of a simulated model of the sample, the analysis comprising:
   spectrally analyzing the spectrum so as to determine one or more characteristic frequencies; and
   fitting the simulated model to the spectrum by an iterative optimization process beginning from an initial condition determined by the one or more characteristic frequencies.

2. The method according to claim 1, wherein measuring the distribution comprises measuring an X-ray reflectance spectrum, and wherein applying the multi-step analysis comprises determining at least one of a thickness, a density and a surface quality of one or more surface layers on the sample.

3. The method according to claim 1, wherein spectrally analyzing the spectrum comprises applying a Fourier Transform analysis method.

4. The method according to claim 1, wherein the iterative optimization process comprises at least one of a gradient-based algorithm and an exhaustive search algorithm.

5. The method according to claim 1, wherein the iterative optimization process comprises a genetic algorithm.

6. The method according to claim 5, wherein fitting the simulated model comprises applying two or more genetic algorithm processes to give respective fitting results, and comprising comparing the respective fitting results in order to determine the physical properties.

7. The method according to claim 1, wherein applying the multi-step analysis comprises reducing a volume of data in the X-ray spectrum so as to generate a compressed spectrum, and then fitting the simulated model to the compressed spectrum.

8. The method according to claim 1, wherein fitting the simulated model comprises applying two or more different FOM (Figure-Of-Merit) functions to the spectrum and to the simulated model.

9. The method according to claim 1, wherein fitting the simulated model comprises applying a FOM (Figure-Of-Merit) function that is corrected for aberrations and statistics of a system used to irradiate the sample and measure the distribution.

10. The method according to claim 1, wherein applying the multi-step analysis comprises exchanging external data with at least one of an optical ellipsometer and an X-ray fluorescence spectrometer.

11. A method for inspection of a sample, comprising:
    irradiating the sample with a beam of X-rays;
    measuring a distribution of the X-rays that are emitted from the sample responsively to the beam, thereby generating an X-ray spectrum; and
    applying a multi-step analysis to the spectrum so as to determine one or more physical properties of simulated models of the sample, the analysis comprising:
    fitting the simulated model to the spectrum by two or more iterative optimization processes so as to generate respective fitting results; and
    comparing the results of the two or more iterative optimization processes to one another so as to determine an output model of the multi-step analysis.

12. The method according to claim 11, wherein fitting the simulated model comprises applying a genetic algorithm.

13. The method according to claim 12, wherein fitting the simulated model comprises applying two or more genetic algorithm processes to give the respective fitting results.

14. The method according to claim 13, wherein comparing the results comprises applying an additional genetic algorithm process to the fitting results, so as to determine the output model.

15. The method according to claim 11, wherein fitting the simulated model comprises applying a different, respective FOM (Figure-Of-Merit) function in each of at least two of the iterative optimization processes.

16. Apparatus for inspection of a sample, comprising:
    an X-ray source, which is arranged to irradiate the sample with a beam of X-rays;
    a detector assembly, which is arranged to measure a distribution of the X-rays that are emitted from the sample responsively to the beam, thereby generating an X-ray spectrum; and
    a processor, which is arranged to spectrally analyze the spectrum so as to determine one or more characteristic frequencies, and to fit a simulated model to the spectrum by an iterative optimization process beginning from an initial condition determined by the one or more characteristic frequencies, thereby determining one or more physical properties of the simulated model of the sample.

17. The apparatus according to claim 16, wherein the detector assembly is arranged to measure the distribution of the X-rays reflected from the sample.

18. The apparatus according to claim 16, wherein processor is arranged to apply a Fourier Transform analysis method in order to determine the one or more characteristic frequencies.

19. The apparatus according to claim 16, wherein the iterative optimization process comprises at least one of a gradient-based algorithm and an exhaustive search algorithm.

20. The apparatus according to claim 16, wherein the iterative optimization process comprises a genetic algorithm.

21. The apparatus according to claim 20, wherein the processor is arranged to apply two or more genetic algorithm processes to give respective fitting results, and to compare the respective fitting results in order to determine the physical properties.

22. The apparatus according to claim 16, wherein the processor is arranged to reduce a volume of data in the X-ray spectrum so as to generate a compressed spectrum, and to fit the simulated model to the compressed spectrum.

23. The apparatus according to claim 16, wherein the processor is arranged to apply two or more different FOM (Figure-Of-Merit) functions to the spectrum and to the simulated model in fitting the simulated model to the spectrum.

24. The apparatus according to claim 16, wherein the processor is arranged to apply a FOM (Figure-Of-Merit) function that is corrected for aberrations and statistics of the apparatus in fitting the simulated model to the spectrum.

25. The apparatus according to claim 16, wherein the processor is arranged to exchange external data with at least one of an optical ellipsometer and an X-ray fluorescence spectrometer.

26. Apparatus for inspection of a sample, comprising:
   an X-ray source, which is arranged to irradiate the sample with a beam of X-rays;
   a detector assembly, which is arranged to measure a distribution of the X-rays that are emitted from the sample responsively to the beam, thereby generating an X-ray spectrum; and
   a processor, which is arranged to fit a simulated model to the spectrum by two or more iterative optimization processes so as to generate respective fitting results and to compare the results of the two or more iterative optimization processes to one another, thereby determining one or more physical properties of the simulated model of the sample.

27. The apparatus according to claim 26, wherein the processor is arranged to fit the simulated model using a genetic algorithm.

28. The apparatus according to claim 27, wherein the processor is arranged to apply two or more genetic algorithm processes to give the respective fitting results.

29. The apparatus according to claim 28, wherein the processor is arranged to apply an additional genetic algorithm process to the fitting results, so as to determine the output model.

30. The apparatus according to claim 26, wherein the processor is arranged to apply a different, respective FOM (Figure-Of-Merit) function in each of at least two of the iterative optimization processes.

* * * * *